United States Patent
Lee et al.

(10) Patent No.: US 8,742,752 B2
(45) Date of Patent: Jun. 3, 2014

(54) NONDESTRUCTIVE INSPECTION METHOD FOR A HEAT EXCHANGER EMPLOYING ADAPTIVE NOISE THRESHOLDING

(75) Inventors: Qui V. Lee, Pittsburgh, PA (US); G. Craig Bowser, North Huntington, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 782 days.

(21) Appl. No.: 12/895,942

(22) Filed: Oct. 1, 2010

(65) Prior Publication Data

US 2012/0081108 A1    Apr. 5, 2012

(51) Int. Cl.
*G01N 27/82* (2006.01)
*G01R 33/12* (2006.01)

(52) U.S. Cl.
USPC ............................ 324/220; 324/222; 324/228

(58) Field of Classification Search
USPC ................................................. 324/228, 220
See application file for complete search history.

(56) References Cited

U.S. PATENT DOCUMENTS

| | | | |
|---|---|---|---|
| 3,302,105 A | 1/1967 | Libby et al. | |
| 3,528,003 A * | 9/1970 | Forster | 324/227 |
| 4,763,274 A | 8/1988 | Junker et al. | |
| 4,876,506 A | 10/1989 | Brown et al. | |
| 5,068,608 A | 11/1991 | Clark, Jr. | |
| 5,365,169 A | 11/1994 | Hosohara et al. | |
| 5,461,312 A | 10/1995 | Hosohara et al. | |
| 6,959,267 B2 | 10/2005 | Le | |
| 7,711,499 B2 | 5/2010 | Junker et al. | |
| 2003/0195710 A1 | 10/2003 | Junker et al. | |
| 2010/0085044 A1 | 4/2010 | Sawawatari | |

OTHER PUBLICATIONS

"Steam Generator Automated Eddy Current Data Analysis: A Benchmarking Study," EPRI, Palo Alto, CA, 1998, TR-111463.
"Measuring and Monitoring Noise in Steam Generator Tubing Eddy-Current Data for Tube Integrity Applications," EPRI, Palo Alto, CA, 2008, 1016554.

* cited by examiner

*Primary Examiner* — Bot Ledynh
(74) *Attorney, Agent, or Firm* — Richard J. Coldren; Westinghouse Electric Company LLC

(57) ABSTRACT

A method of eddy current testing for flaws in a tube is provided that includes passing an eddy current probe through the tube and obtaining eddy current data for a number of positions along the tube, analyzing the eddy current data to generate background noise data for a number of positions along the tube, analyzing the eddy current data to generate extracted data for a number of positions along the tube, and determining whether a flaw of a particular category is present in the tube based on a set of one or more of rules applied to at least a portion of the extracted data, wherein at least one of the rules uses a particular part of the extracted data and employs a threshold that is a function a particular part of the background noise data that is associated with the particular part of the extracted data.

18 Claims, 3 Drawing Sheets

NONDESTRUCTIVE INSPECTION METHOD FOR A HEAT EXCHANGER EMPLOYING ADAPTIVE NOISE THRESHOLDING

BACKGROUND OF THE INVENTION

1. Field of the Invention

The present invention relates to a method of inspecting a heat exchanger comprising a plurality of tubes, and in particular to a nondestructive method of inspecting heat exchanger tubes that employs adaptive thresholding based on noise.

2. Related Art

Heat exchangers, such as, for example, steam generators used in pressurized water nuclear powered electric generating systems, generally include thousands of U-shaped heat exchanger tubes disposed within a generally cylindrical pressure vessel. The ends of the heat exchanger tubes are secured within a transverse plate called a tubesheet, which separates the steam generator into a primary side and a secondary side. Heated primary fluid from the nuclear reactor is passed through the tubes to effectuate a heat transfer with the secondary working fluid which, in turn, drives the turbo-machinery used to generate electricity. The primary fluid can be radioactive. Accordingly, to prevent leakage of the reactor coolant into the secondary side of the generator, which would contaminate the steam, the heat transfer tubes must be periodically inspected for flaws and degradation such as cracks, pits, dents and tube wall thinning. If a degraded tube is discovered, it is typically plugged at both ends. In view of the thousands of tubes in the steam generator, plugging of a few tubes does not appreciably affect the efficiency of the heat transfer.

Eddy current testing is a well known, commonly used method of nondestructive testing of steam generator tubes. Generally, in performing an eddy current test on steam generator tubes, a sensor or probe is advanced through the tube as signals are generated and recorded for later analysis. See, e.g., U.S. Pat. No. 3,302,105 (illustrating and describing the eddy current signatures of various types of tube defects); see also U.S. Pat. Nos. 3,693,075; 4,194,149; 4,207,520; and 4,631,688. U.S. Pat. No. 4,763,274, which was filed on Jun. 24, 1986 and issued to the assignee hereof, discloses eddy current inspection processes for nuclear steam generator tubes and computer analysis of the eddy current data for automatically detecting flaws in the heat transfer tubes of a steam generator.

Automatic analysis systems employ what is commonly known as flaw categorization, which is a process wherein the eddy current data that is collected is analyzed flaws in the tube are identified and categorized based on a set of logic based rules. The logic based rules typically employ a set of minimum thresholds that are defined by an analyst. A low fixed threshold may create a large number of false positive reports on noisy tubes, and a high fixed threshold may lead to certain flaw signals not being addressed or properly categorized.

Thus, there is a need for an improved nondestructive method of inspecting heat exchanger tubes that addresses the problems associated with minimum thresholds described above.

SUMMARY OF THE INVENTION

In one embodiment, a method of eddy current testing for flaws in a tube is provided that includes passing an eddy current probe through the tube and obtaining eddy current data for a number of positions along the tube, analyzing the eddy current data to generate background noise data for a number of positions along the tube, analyzing the eddy current data to generate extracted data for a number of positions along the tube, and determining whether a flaw of a particular category is present in the tube based on a set of one or more of rules applied to at least a portion of the extracted data, wherein at least one of the rules uses a particular part of the extracted data and employs a threshold that is a function a particular part of the background noise data that is associated with the particular part of the extracted data.

In another embodiment, a system is provided that includes an eddy current probe mechanism structured to obtain eddy current data for a number of positions along the tube, and a computer system having a processing unit comprising a processor and a memory device, wherein the memory device stores one or more routines executable by the processor, the one or more routines including instructions for implementing the method just described.

In still another embodiment, a method of eddy current testing for flaws in a tube includes passing an eddy current probe through the tube and obtaining eddy current data for a number of positions along the tube, analyzing the eddy current data to generate extracted data for a number of positions along the tube, and determining whether a flaw of a particular category is present in the tube based on a set of one or more of rules applied to at least a portion of the extracted data, wherein at least one of the rules employs a threshold, wherein a value of the threshold is adjusted according to a repeating pattern based on a position along the tube.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

A further understanding of the invention can be gained from the following description of the preferred embodiments when read in conjunction with accompanying drawings in which.

DESCRIPTION OF THE PREFERRED EMBODIMENT

Figure 1:
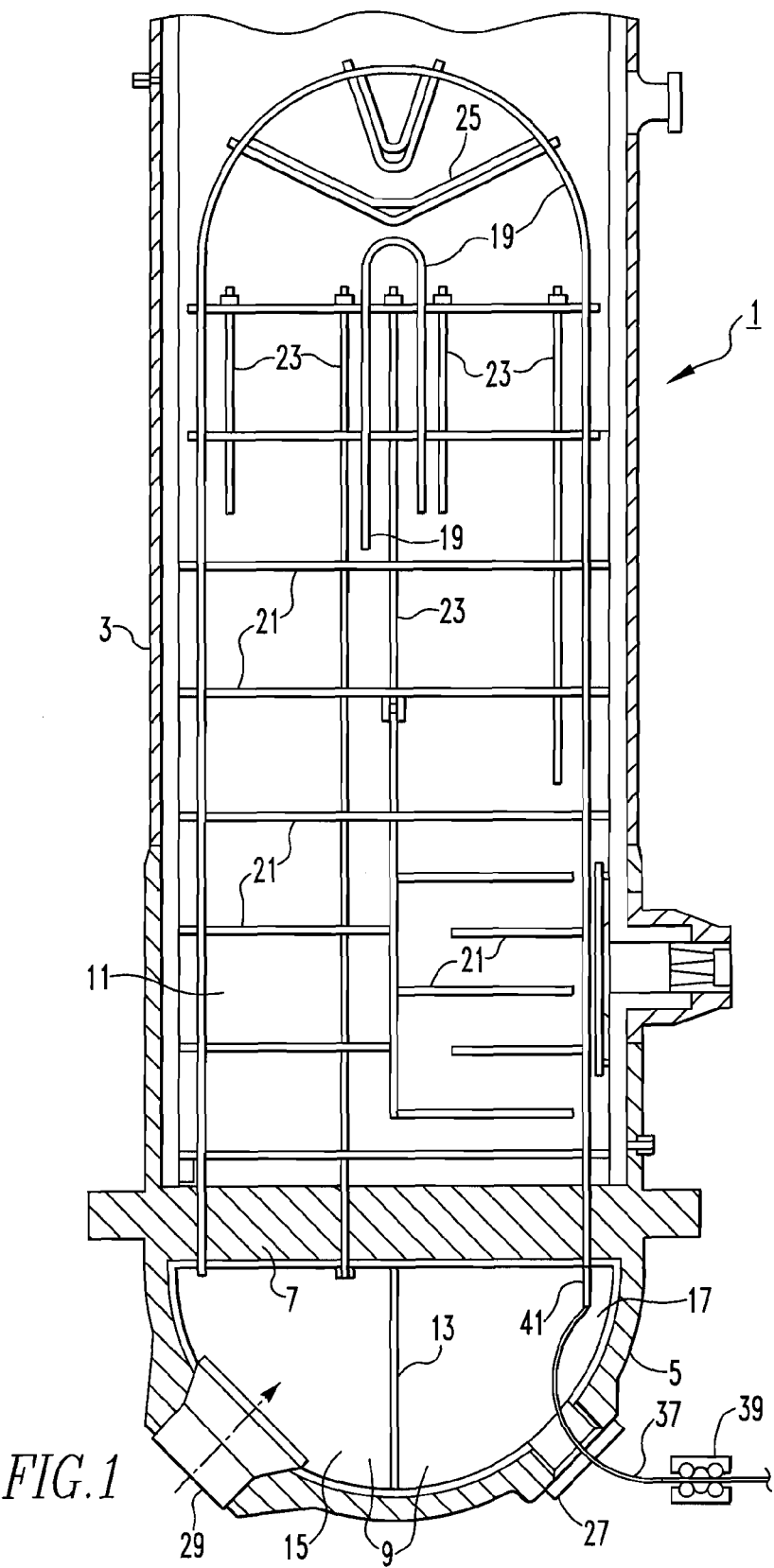
FIG. 1 is a schematic diagram of a typical steam generator which forms part of the nuclear steam supply system in a pressurized water reactor electric power generating plant.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

The invention will be described as applied to analysis of eddy current data generated from an inspection of steam generator 1 shown in FIG. 1, which is a typical steam generator which forms part of the nuclear steam supply system in a pressurized water reactor electric power generating plant. Steam generator 1 comprises cylindrical body portion 3 which is fitted at its lower end with hemispherical shell 5. Tube sheet 7 at the lower end of cylindrical body portion 3 divides steam generator 1 into primary side 9 below tube sheet 7 and secondary side 11 above tube sheet 7. Primary side 9, which is also referred to as the channel head, is divided in half by vertical divider plate 13 into inlet section 15 and outlet section 17. Thousands of U-shaped tubes 19 (only parts of two shown for clarity) are mounted in secondary side 11 with one end extending through tube sheet 7 into the inlet section 15 and the other into outlet section 17 of the channel head 9. Tubes 19 are supported on secondary side 11 of the generator by a series of metal support plates 21 braced by tie rods 23, and by antivibration bars 25. Access can be gained to the tubes 19 through a manway 27. Primary side water enters steam generator 1 through inlet nozzle 29 and travels through tubes 19 to outlet side 17.

Figure 2:
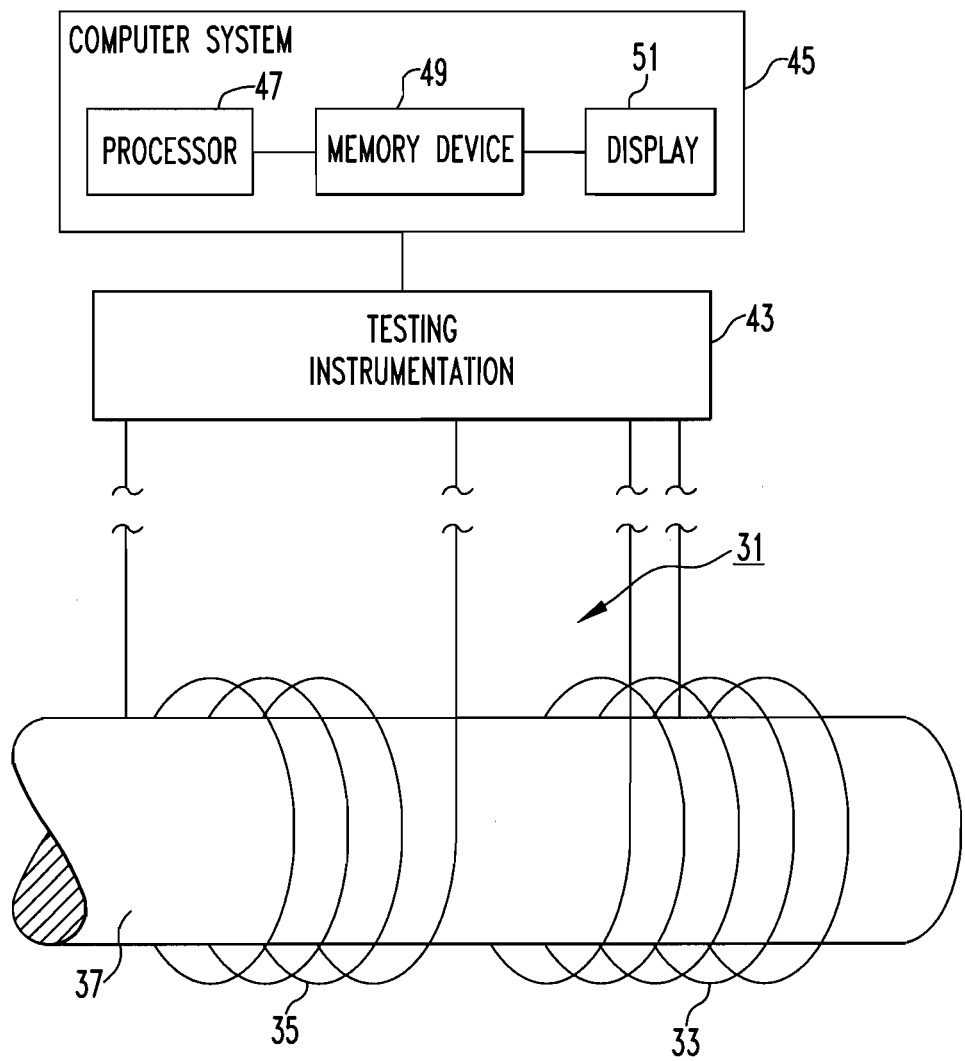
FIG. 2 is a schematic diagram of a probe, testing instrumentation and computer system used for obtaining eddy current data from the tubes of the steam generator shown in FIG. 1.

In performing an inspection of tubes 19 of steam generator 1, probe 31 in the form of a pair of differentially wound coils 33 and 35, as schematically shown in FIG. 2, is mounted on the end of a long flexible non-electromagnetically active rod 37 which is inserted sequentially into each of tubes 19 to be inspected.

As shown in FIG. 1, rod 37 carrying probe 31 is fed into and out of the selected tube 19 by drive mechanism 39. As rod 37 is withdrawn from a tube 19, coils 33 and 35 are sequentially multiplexed at multiple frequencies, typically 400 KHz, 200 KHz, 100 KHz and 10 KHz. For the differential signals, measurements are taken from the oppositely wound coils 33 and 35 measured simultaneously. For the absolute signals, a measurement is taken from only one of the coils and this signal is compared with that generated in an external reference coil (not shown). Data is taken a number of times per second (e.g., 400 times per second). That is, the sequence of 4 differential signals and 4 absolute signals is repeated every certain number of milliseconds (e.g., every 2.5 milliseconds). In addition, probe 31 is withdrawn from the tube 19 at a certain nominal speed. For example, probe 31 may be withdrawn at a nominal speed of 1 foot per second so that the data points are about 0.03 inches apart.

As is well known in the field of eddy current testing, variations in the characteristics of the tubes 19 such as dents, and flaws, such as pitting, cracks, and thinning, in the walls, as well as the presence of adjacent structures such as support plates 21, tube sheet 7 and antivibration bars 25, influence the effective impedance of probe coils 33 and 35. In order to calibrate the system, a test section of tube 41 is connected to the end of a selected tube 19 so that the probe must pass through the test section as well as the tube to be tested. The test section 41 is provided with standard flaws in the form of 20%, 40%, 60%, and 100% through wall holes of specified diameter, and a standard ring which surrounds the tube and generates an indication similar to that of a support plate 21. The signals generated by these test features are also recorded.

The signals generated by probe 31 as probe 31 is moved along a tube 19 are supplied to testing instrumentation 43 (FIG. 2). Testing instrumentation 43 digitizes the signals generated by probe 31 to create multiple channels of data, wherein each channel of data can provide voltage (amplitude of the signal) or phase (angle of the signal with respect to a reference) information for any of the multiple frequencies being employed. Probe 31 is operatively coupled to computer system 45, which receives the digital data from testing instrumentation 43. Computer system 41 includes a processing unit having processor 47, which may be a microprocessor or microcontroller, and memory device 49. Computer 45 also includes display 51, which in the exemplary embodiment is a computer screen. The exemplary memory device 49 includes database management software for recording the data described herein. The exemplary memory device 49 also stores one or more software routines executable by processor 47 for carrying out the steps of the method described herein and shown in FIG. 3.

Figure 3:
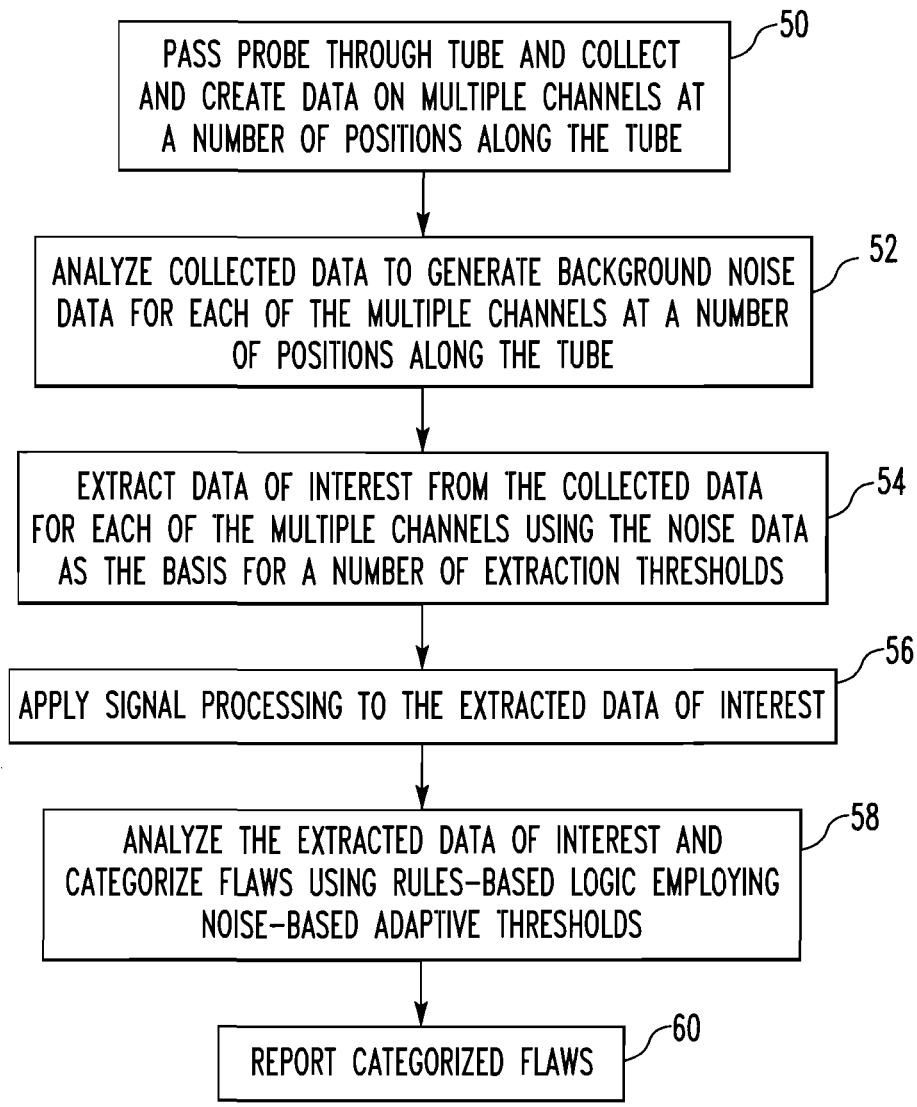
FIG. 3 is a flowchart illustrating a method of inspecting a heat exchanger tube and categorizing flaws therein according to an exemplary embodiment of the present invention.

FIG. 3 is a flowchart illustrating a method of inspecting a heat exchanger tube and categorizing flaws according to an exemplary embodiment of the present invention. In one, non-limiting illustrative embodiment used herein for describing the present invention, the method of FIG. 3 may be implemented in steam generator 1 shown in FIG. 1 using probe 31, testing instrumentation 43 and computer system 45 shown in FIG. 2. It should be understood, however, that the method may be implemented in other heat exchanger environments using other hardware configurations without departing from the scope of the present invention.

Referring to FIG. 3, the method begins at step 50, wherein probe 31 is passed through and along a tube 19, during which time eddy current signals are generated as described elsewhere herein. Those signals are provided to testing instrumentation 43, which digitizes the eddy current signals and creates digital data based thereon on a number of channels of interest for each of a number of positions along the tube depending on the sampling rate of probe 31, the sampling rate of the A/D converter of testing instrumentation 43, and the rate at which probe 31 is moved. For example, the data points may by 0.03 inches apart. As described elsewhere herein, each of those channels will comprise voltage or phase data for a number of different frequencies. The channel data is then provided to computer system 45.

Next, at step 43, computer system 45 analyzes the collected channels to generate background noise data for each of the number of channels of interest at a number of positions along the tube 19. For example, background noise data may be measured/generated every 0.5 inches along the tube length. In one particular, non limiting exemplary embodiment, the tube 19 is broken up into a number of different regions of interest, and the frequency at which background noise data is measured/generated is different for each region of interest. In this embodiment, the regions of interest are the support plate region, the free span region (which is between the support plates), the U-bend region, the tubesheet region, and the anitvibration bar region. In the free span region, background noise data is measured/generated for a 0.5 inch window of the tube 19 that is moved in 0.3 inch increments, although those values may be adjusted. The U-bend region, the tubesheet region, the support plate region and the anitvibration bar region are referred to as supporting structure regions, and the background noise in those regions may be measured with respect to the center, edges or full length of the supporting structures thereof. The noise data measured/generated in each case will be appropriate for the channel in question (i.e., voltage or phase measured as appropriate). The background noise data, however measured/generated from the collected data in the number of channels of interest, is stored by memory device 49 of computer system 45.

Next, at step 54, computer system 45 extracts data of interest from the collected data in each of the number of channels of interest using the background noise data as the basis for a number of extraction thresholds, such that only data that exceeds these extraction thresholds will be extracted for later use. The extraction thresholds can be determined based on the nature/source of the noise components and its contribution to total noise. In the exemplary embodiment, computer system 45 does so by examining each piece of data in the number of channels of interest and comparing it to an extraction threshold value, wherein the extraction threshold value is some predetermined value above the background noise data that corresponds to the piece of data being examined (e.g., background noise data+some %). The background noise data that corresponds to the piece of data being examined may be a localized noise value (noise in a small window around the signal of interest such as 5 inches). Alternatively, the background noise data that corresponds to the piece of data being examined may be a regional noise value (noise for that particular region of interest) for that tube. These regional noise values could come from hundred of inches in a free span section or from several structure edges or structure centers. If appropriate, sampling noise values in adjacent tubes could be used to enhance the noise input process in the evaluation. Usually, the background noise consists of tube manufacturing noise and instrumentation noise. While the instrumentation noise is consistent and expected at certain values, the tube manufacturing noise is not as one tube may have several times of the noise level as compared to another tube. Part of noise analysis is to determine the noise sources, and its characteristic to apply proper extraction. It is also important to understand the noise contribution from service conditions (scale, deposits, etc.) that must be separated from total noise values so appropriate extraction would be effective. The system can refer to manufacturing raw eddy current data to determine the manufacturing noise if not already stored in the database. If the piece of data being examined exceeds the extraction threshold value computed from that tube background noise, it will be considered extracted data of interest for further consideration as described below.

At step 56, one or more signal processing techniques is applied to the extracted data of interest in each of the number of channels of interest in order to condition the data for further processing. For example, as is known in the art, certain signals may be mixed (suppressed) in a manner that eliminates signals relating to support plates 21 and enhances signals related to degradation. Other signal processing such as filters can be used.

At step 58, the extracted data of interest in each of the number of channels of interest is analyzed by computer 45 in order to categorize flaws in the tube 19 using rules-based logic employing noise-based adaptive thresholds as described below. More specifically, computer system 45 implements an automated analysis and flaw categorization system (software routines are stored in memory device 49 and executed by processor 47) wherein a number of different predetermined flaw categories will be pre-established. For example, the flaw categories may specify wear, pitting, cracks, or what is commonly referred to as NQI (non-quantified indications). Each flaw category is defined by a set of rules logic, and rules logic will have its own number of individual rules that each must be satisfied to conclude that the flaw is present. Also, each rule in the set will specify a data type (voltage or phase from a particular channel) and a minimum threshold (e.g., 0.15V or 30 degrees) and a maximum threshold (e.g., 1000.0V or 150 degrees) in which the data must fall to satisfy the rule. Usually, if even one rule in the set is not satisfied, the set is deemed failed and the flaw will be found not to be present. Thus, the extracted data of interest in each of the number of channels of interest can be examined using the analysis and flaw categorization system and in particular the rules logic at various positions along the tube to determine whether flaws should be identified and reported.

According to the present invention, in one or more of the individual rules, the minimum threshold is a function of the measured/generated background noise for that channel and for that position of the tube 19 so that it will change rather than being static. The background noise data that is used in the rules at any particular time may be a localized noise value (noise in a small window around the signal of interest such as 5 inches). Alternatively, the background noise data may be a regional noise value (noise for that particular region of interest) for that tube. These regional noise value could come from hundred of inches in a free span section or from several structure edges or structure centers. If appropriate, sampling noise values in adjacent tubes could be used to enhance the noise input process in the evaluation. For example, the minimum threshold for a rule might be specified as a range of 0.15V to (2*Background Noise), so if Background Noise was 0.01V, then the minimum threshold would be 0.02V (if the data is noisy, and (2*Background Noise) is higher than 0.15V, then 0.15V will be used by the rule; the rule is bounded by 0.15V, so that a small flaw of 0.15V will not be missed because of high background noise). Similarly, the minimum threshold for a rule might be 30 deg, and if Background Noise was 5 deg, then this phase noise of 5 deg could be used for signal transformation and measurement in the evaluation/ categorization process. Alternatively, phase angles may simply be added or subtracted during the adaptive thresholding during flaw categorization In one exemplary embodiment, a rule for flaw categorization may also specify a particular repeating pattern that a voltage or phase should follow on a particular channel (that pattern could would be stored in memory device 49). The pattern will then be used to determine if adaptive threshold technique can be used. Its level of adaptive threshold will depend on whether and how much of the signal follows certain noise pattern. [For example, in the case of a pilgered tube, a pattern of pilger signals would be created that would repeat at a regular interval (about every 2 to 3 inches). That would also present a regular repeating pattern of voltage and phase noise throughout the tube, wherein the noise would only be present periodically. For example, there may be 0.5-2.0 V and 170 degrees of noise that repeats every two to three inches for hundreds of inches along the tube. Thus, in the rules-based logic, the threshold would only need to be adjusted for that noise periodically, i.e., when the periodic noise is present, and not or less when the periodic noise is not present.

Following step 58, once all of the extracted data of interest has been analyzed and all of the flaws have been categorized, the flaws may be reported as shown in step 60.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the breath of the appended claims and any and all equivalents thereof.

What is claimed is:

1. A method of eddy current testing for flaws in a tube, comprising:
   passing an eddy current probe through the tube and obtaining eddy current data for a first number of positions along the tube;
   analyzing the eddy current data to generate background noise data for a second number of positions along the tube, the background noise data comprising a plurality of noise data values wherein each of the noise data values is associated with a respective one of the second number of positions;
   analyzing the eddy current data to generate extracted data for a third number of positions along the tube; and
   determining whether a flaw of a particular category is present in the tube based on a set of one or more of rules applied to at least a portion of the extracted data, wherein at least one of the rules uses a particular part of the extracted data and employs a changing threshold that changes with position along the tube and that, for any selected position along the tube, is a function of a particular one of the noise data values that is associated with the selected position along the tube.

2. The method according to claim 1, wherein the analyzing the eddy current data to generate extracted data comprises using the eddy current data and the background noise data to generate the extracted data.

3. The method according to claim 2, wherein the background noise data is used to create one or more extraction thresholds for generating the extracted data from the eddy current data.

4. The method according to claim 3, wherein the generating the extracted data from the eddy current data comprises comparing each piece of the eddy current data to one of the extraction thresholds to determine whether the piece of eddy current date should be considered to be extracted data.

5. The method according to claim 1, wherein the particular part of the extracted data and each of the particular ones of the noise data values are each a voltage.

6. The method according to claim 1, wherein the particular part of the extracted data and each of the particular ones of the noise data values are each a phase angle.

7. The method according to claim 1, wherein at least one of the particular ones of the noise data values is a localized noise value associated with a predetermined local portion of the tube.

8. The method according to claim 1, wherein at least one of the particular ones of the noise data values is a regional noise value associated with a particular region of the tube.

9. A system for eddy current testing for flaws in a tube, comprising:
   an eddy current probe mechanism structured to obtain eddy current data for a first number of positions along the tube; and
   a computer system having a processing unit comprising a processor and a memory device, wherein the memory device stores one or more routines executable by the processor, the one or more routines including instructions for:
   analyzing the eddy current data to generate background noise data for a second number of positions along the tube, the background noise data comprising a plurality of noise data values wherein each of the noise data values is associated with a respective one of the second number of positions;
   analyzing the eddy current data to generate extracted data for a third number of positions along the tube; and
   determining whether a flaw of a particular category is present in the tube based on a set of one or more of rules applied to at least a portion of the extracted data, wherein at least one of the rules uses a particular part of the extracted data and employs a changing threshold that changes with position along the tube and that, for any selected position along the tube, is a function of a particular one of the noise data values that is associated with the selected position along the tube.

10. The system according to claim 9, wherein the instructions for analyzing the eddy current data to generate extracted data include instructions for using the eddy current data and the background noise data to generate the extracted data.

11. The system according to claim 10, wherein the background noise data is used to create one or more extraction thresholds for generating the extracted data from the eddy current data.

12. The system according to claim 11, wherein the generating the extracted data from the eddy current data comprises instructions for comparing each piece of the eddy current data to one of the extraction thresholds to determine whether the piece of eddy current date should be considered to be extracted data.

13. The system according to claim 9, wherein the particular part of the extracted data and each of the particular ones of the noise data values are each a voltage.

14. The system according to claim 9, wherein the particular part of the extracted data and each of the particular ones of the noise data values are each a phase angle.

15. The system according to claim 9, wherein at least one of the particular ones of the noise data values is a localized noise value associated with a predetermined local portion of the tube.

16. The system according to claim 9, wherein at least one of the particular ones of the noise data values is a regional noise value associated with a particular region of the tube.

17. The system according to claim 9, wherein the eddy current probe mechanism comprises and eddy current probe (31) having a pair of differential coils (33, 350) coupled to testing instrumentation (43) adapted to digitize a signal generated by the eddy current probe.

18. A method of eddy current testing for flaws in a tube, comprising:
   passing an eddy current probe through the tube and obtaining eddy current data for a number of positions along the tube;
   analyzing the eddy current data to generate extracted data for a number of positions along the tube; and
   determining whether a flaw of a particular category is present in the tube based on a set of one or more of rules applied to at least a portion of the extracted data, wherein at least one of the rules employs a changing threshold, wherein a value of the threshold is adjusted according to a repeating pattern based on a position along the tube.

* * * * *